United States Patent
Lin et al.

(10) Patent No.: US 11,679,076 B2
(45) Date of Patent: Jun. 20, 2023

(54) COMPOSITION FOR SUBMUCOSAL INJECTION AND PREPARATION METHOD THEREOF

(71) Applicant: T-ACE Medical Co., Ltd., Tainan (TW)

(72) Inventors: Chih-Chiang Lin, Tainan (TW); Chun-Yao Huang, Tainan (TW); Hung-En Wei, Tainan (TW); Hui-Fang Li, Tainan (TW)

(73) Assignee: T-ACE Medical Co., Ltd., Tainan (TW)

( * ) Notice: Subject to any disclaimer, the term of this patent is extended or adjusted under 35 U.S.C. 154(b) by 222 days.

(21) Appl. No.: 17/180,917

(22) Filed: Feb. 22, 2021

(65) Prior Publication Data

US 2022/0040091 A1 Feb. 10, 2022

Related U.S. Application Data

(60) Provisional application No. 63/061,810, filed on Aug. 6, 2020.

(51) Int. Cl.
| | |
|---|---|
| A61K 9/00 | (2006.01) |
| A61K 31/721 | (2006.01) |
| A61K 31/723 | (2006.01) |
| A61K 31/734 | (2006.01) |
| A61K 9/14 | (2006.01) |
| C08B 37/00 | (2006.01) |

(52) U.S. Cl.
CPC .......... *A61K 9/0019* (2013.01); *A61K 31/721* (2013.01); *A61K 31/723* (2013.01); *A61K 31/734* (2013.01); *C08B 37/0033* (2013.01); *C08B 37/0084* (2013.01); *C08B 37/0096* (2013.01); *A61K 9/14* (2013.01)

(58) Field of Classification Search
CPC .......................... A61K 9/0019; A61K 31/702
See application file for complete search history.

(56) References Cited

U.S. PATENT DOCUMENTS

2016/0346430 A1* 12/2016 Nagale ................ A61L 27/20

* cited by examiner

*Primary Examiner* — Michael B. Pallay
(74) *Attorney, Agent, or Firm* — Chieh-Mei Wang

(57) ABSTRACT

The present disclosure provides a composition for submucosal injection including a divalent cation and an oligosaccharide obtained by exposing powdered polysaccharides to irradiation, heat, ultrasound, or ultraviolet radiation. The composition may be provided as a single solution; or the divalent cation and the oligosaccharide may be separately packaged, with the divalent cation being provided in solution form and the oligosaccharide being provided in powder form. The divalent cation may be 0.1-0.5% w/v of $Ca^{2+}$, $Mg^{2+}$, $Fe^{2+}$, $Cu^{2+}$, $Ba^{2+}$, $Zn^{2+}$, or any combination thereof. The oligosaccharide may be 0.5-2% w/v of degraded sodium alginate, degraded xanthan gum, degraded dextran, degraded welan gum, degraded gellan gum, degraded diutan gum, or any combination thereof. When the divalent cation is in contact with the oligosaccharide, viscosity of the composition is greater than 1000 cP, and injection pressure of the composition falls within a range of 2.5-4 kgf.

20 Claims, 4 Drawing Sheets

COMPOSITION FOR SUBMUCOSAL INJECTION AND PREPARATION METHOD THEREOF

REFERENCE TO RELATED APPLICATION

This application claims the benefit of U.S. provisional patent application No. 63/061,810, filed on Aug. 6, 2020, the entirety of which is incorporated herein by reference.

FIELD OF THE DISCLOSURE

The present disclosure relates to a composition for submucosal injection, and more particularly to a pseudoplastic submucosal injection formula and method for preparing the same.

BACKGROUND OF THE DISCLOSURE

Endoscopic resection is a useful therapeutic tool for treating mucosal lesions and early cancers of the gastrointestinal tract, and generally includes endoscopic mucosal resection (EMR) and endoscopic submucosal dissection (ESD). The current standard for conducting an EMR or ESD is to inject a submucosal injection agent into the mucosal layer to uplift or protrude the lesion, so as to cause a cushion in order to increase the efficiency of lesion removal. Common submucosal injection agents typically include saline, glycerin, hyaluronic acid, glucose, and hydroxypropyl methylcellulose.

However, since saline tends to diffuse when injected into a tissue, especially with the added pressure created by the resection, the cushion deforms and disappears within a short period of time; therefore, repeated injection of saline is required in order to maintain the cushion.

Furthermore, current submucosal injection agents include two separate solutions, one of which contains polysaccharides and the other contains divalent cations. When used clinically, the two solutions are separately injected into the lesion to allow the polysaccharides and divalent cations to cross-link and form an insoluble colloid at the site of lesion. If the solutions are combined prior to injection, the insoluble colloid would block the endoscope injection needle, thus making the injection impossible.

SUMMARY OF THE DISCLOSURE

An objective of the present disclosure is to provide a submucosal injection agent that possesses the following properties: (1) long-lasting submucosal cushioning, (2) safe and non-toxic, (3) readily available, (4) easy to inject, and (5) non damaging to the tissue.

An objective of the present disclosure is to provide a pseudoplastic submucosal injection agent that is low in injection pressure and high in tissue uplifting efficiency.

An embodiment of the present disclosure provides a composition for submucosal injection that includes a divalent cation and an oligosaccharide. When the divalent cation is in contact with the oligosaccharide, viscosity of the composition is greater than 1000 cP and injection pressure of the composition falls within a range of 2.5-4 kgf.

In an embodiment, the oligosaccharide in the composition is obtained by exposing powdered polysaccharides to irradiation, heat, ultrasound, or ultraviolet radiation.

In an embodiment, the oligosaccharide in the composition is obtained by exposing powdered polysaccharides to 25-100 kGy of gamma ($\gamma$) irradiation, 160-200° C. of heat, 100-280 nm of UV-C light, or 20-60 kHz of ultrasound.

In an embodiment, the divalent cation in the composition includes at least one cation selected from $Ca^{2+}$, $Mg^{2+}$, $Fe^{2+}$, $Cu^{2+}$, $Ba^{2+}$, and $Zn^{2+}$.

In an embodiment, the concentration of the divalent cation in the composition falls within the range of 0.1-0.5% w/v.

In an embodiment, the oligosaccharide in the composition includes at least one member selected from degraded sodium alginate, degraded xanthan gum, degraded dextran, degraded welan gum, degraded gellan gum, and degraded diutan gum.

In an embodiment, a concentration of the oligosaccharide in the composition falls within a range of 0.5-2% w/v.

In the embodiment, the divalent cation and the oligosaccharide are pre-mixed and provided as a single solution.

In an embodiment, the divalent cation and the oligosaccharide are separately packaged, and the oligosaccharide is provided in powder form.

In an embodiment, the composition further includes a physiologically acceptable excipient.

Another embodiment of the present disclosure provides a method for preparing the aforementioned composition for submucosal injection. The method includes the steps of: providing a divalent cation solution; providing an oligosaccharide in powder form; and mixing the oligosaccharide with the solution to obtain the composition.

Yet another embodiment of the present disclosure provides a use of the aforementioned composition in preparation of a medicament for submucosal elevation.

The composition for submucosal injection according to the embodiments of the present disclosure is easy to use and shows low injection pressure and excellent submucosal elevation capacity.

For making the above and other purposes, features and benefits become more readily apparent to those ordinarily skilled in the art, the preferred embodiments and the detailed descriptions with accompanying drawings will be put forward in the following descriptions.

BRIEF DESCRIPTION OF THE DRAWINGS

The present disclosure will become more readily apparent to those ordinarily skilled in the art after reviewing the following detailed description and accompanying drawings, in which.

DETAILED DESCRIPTION OF PREFERRED EMBODIMENTS

Figure 1:
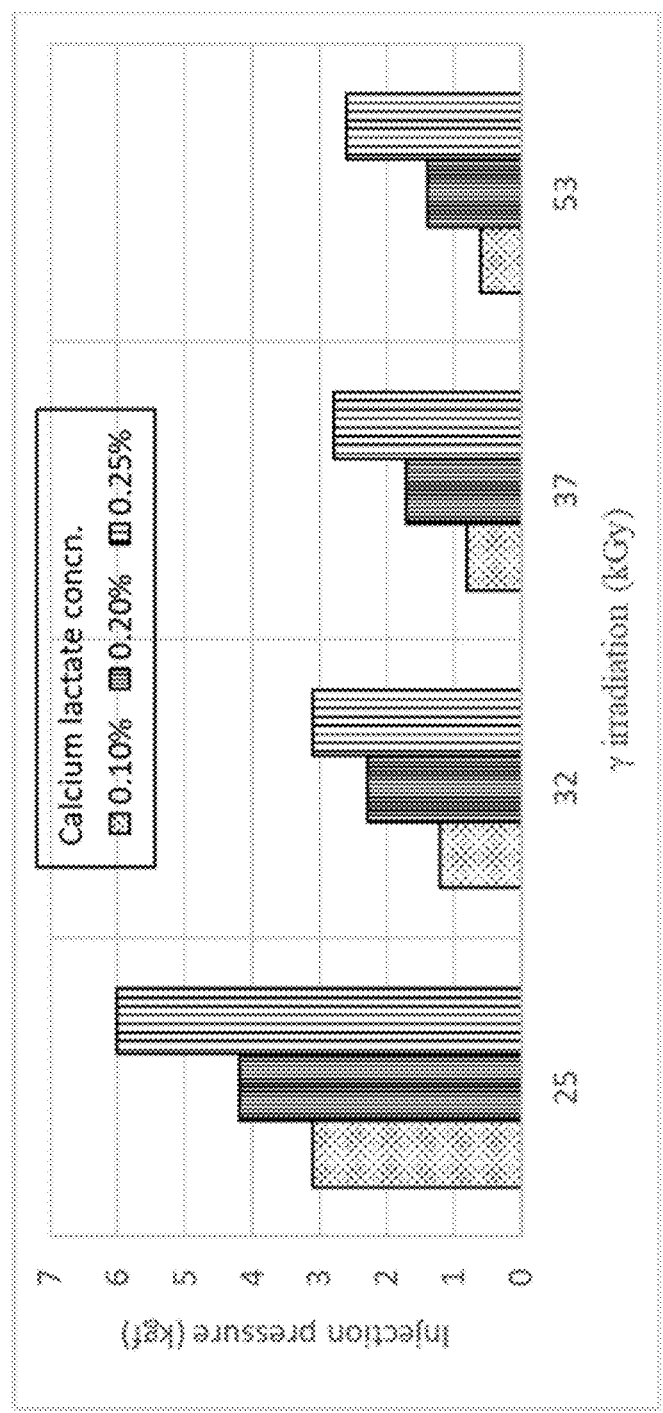
FIG. 1 is a bar chart showing the effect of divalent cation concentration and irradiation dose on injection pressure of the compositions in accordance with embodiments of the present disclosure.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

According to an embodiment of the present disclosure, a composition for submucosal injection includes a divalent cation and an oligosaccharide. The divalent cation and the oligosaccharide may be pre-mixed and provided as a single solution. Alternatively, the divalent cation and the oligosaccharide may be separately packaged, with the divalent cation being provided in solution form (e.g., as a divalent cation solution) and the oligosaccharide being provided in powder form (e.g., as an oligosaccharide powder).

The divalent cation may include at least one divalent cation selected from the group consisting of $Ca^{2+}$, $Mg^{2+}$, $Fe^{2+}$, $Cu^{2+}$, $Ba^{2+}$, and $Zn^{2+}$; in other words, the divalent cation may include $Ca^{2+}$, $Mg^{2+}$, $Fe^{2+}$, $Cu^{2+}$, $Ba^{2+}$, $Zn^{2+}$, or any combination thereof. The oligosaccharide may include at least one member selected from the group consisting of degraded sodium alginate, degraded xanthan gum, degraded dextran, degraded welan gum, degraded gellan gum, and degraded diutan gum; in other words, the oligosaccharide may include degraded sodium alginate, degraded xanthan gum, degraded dextran, degraded welan gum, degraded gellan gum, degraded diutan gum, or any combination thereof.

In the embodiment, the concentration of divalent cation in the composition or the divalent cation solution may fall within the range of 0.1-0.5% w/v. The composition or the divalent cation solution may further include at least one physiologically acceptable excipient (e.g., mannitol) for the divalent cation. A dye (e.g., Brilliant Blue FCF) may also be added to the composition to facilitate visualization of the site of injection.

The concentration of oligosaccharides in the composition may fall within the range of 0.5-2% w/v. The composition or the oligosaccharide powder may further include at least one physiologically acceptable excipient (e.g., sorbitol, sucrose, lactose, maltose, and trehalose).

The oligosaccharide powder or the oligosaccharide in the composition may be obtained from degradation of polysaccharides, which may be achieved by exposing powdered polysaccharides to irradiation, heat, ultrasound, or ultraviolet (UV) radiation. For example, gamma (γ) rays at the dose of 25-100 kGy may be generated from a $^{60}Co$ source to treat the powdered polysaccharides under air atmosphere. In some embodiments, the powdered polysaccharide may be heated in an oven at 160-200° C. for 2-6 h under air atmosphere, or be exposed to 100-280 nm of UV-C light for 1-30 min under air atmosphere, or be suspended in ethanol or other organic solvents and applied an ultrasound at the frequency of 20-60 kHz for 20-200 min under air atmosphere.

In the embodiment, when provided as a single solution, the composition is a homogeneous fluid that exhibits a non-Newtonian pseudoplastic behavior, in which viscosity of the composition is greater than 1000 cP and injection pressure of the composition falls within the range of 2.5-4 kgf. Alternatively, when the divalent cation and the oligosaccharide are separately packaged, the composition would form a homogeneous fluid that exhibits the aforementioned non-Newtonian pseudoplastic behavior once the divalent cation solution is mixed with the oligosaccharide powder.

According to another embodiment of the present disclosure, the aforementioned composition is used in preparation of a medicament for submucosal elevation.

According to yet another embodiment of the present disclosure, a method for preparing the aforementioned composition for submucosal injection includes the steps of: providing a divalent cation solution containing the aforementioned divalent cation; providing the aforementioned oligosaccharide powder; and mixing the oligosaccharide powder with the divalent cation solution to obtain the composition for submucosal injection.

EXAMPLES

Material Preparation

Compositions 1-5: A divalent cation solution is prepared by mixing 0.01-0.03 g of calcium lactate (as detailed in Table 1 below), 0.2 g of mannitol, and 0.002 g of Brilliant Blue FCF in $dH_2O$, and adding $dH_2O$ until the total volume reaches 10 ml. An oligosaccharide powder is prepared by mixing 0.1 g of degraded sodium alginate, 0.25 g of sucrose, and 0.45 g of sorbitol; the sodium alginate is degraded by exposing powdered sodium alginate to 37 kGy of gamma (γ) irradiation. 0.8 g of the oligosaccharide powder is gradually added to 10 ml of the divalent cation solution, and stirred for 15 min at room temperature to obtain compositions 1-5 for submucosal injection.

TABLE 1

| Composition | calcium lactate (g) | calcium lactate concentration (% w/v) |
|---|---|---|
| 1 | 0.01 | 0.1% |
| 2 | 0.015 | 0.15% |
| 3 | 0.02 | 0.2% |
| 4 | 0.025 | 0.25% |
| 5 | 0.03 | 0.3% |

Compositions 6-8: A divalent cation solution is prepared by mixing 0.025 g of calcium lactate, 0.2 g of mannitol, and 0.002 g of Brilliant Blue FCF in $dH_2O$, and adding $dH_2O$ until the total volume reaches 10 ml. An oligosaccharide powder is prepared by mixing 0.1 g of degraded sodium alginate, 0.25 g of sucrose, and 0.45 g of sorbitol; the sodium alginate is degraded by exposing powdered sodium alginate to 25-53 kGy of γ irradiation (as detailed in Table 2 below). 0.8 g of the oligosaccharide powder is gradually added to 10 ml of the divalent cation solution, and stirred for 15 min at room temperature to obtain compositions 6-8 for submucosal injection.

TABLE 2

| Composition | calcium lactate (g) | γ irradiation dose (kGy) |
|---|---|---|
| 4 | 0.01 | 37 |
| 6 | 0.015 | 25 |
| 7 | 0.02 | 32 |
| 8 | 0.025 | 53 |

Compositions 9-14: A divalent cation solution is prepared by mixing 0.01-0.025 g of calcium lactate (as detailed in Table 3 below), 0.2 g of mannitol, and 0.002 g of Brilliant Blue FCF in $dH_2O$, and adding $dH_2O$ until the total volume reaches 10 ml. An oligosaccharide powder is prepared by mixing 0.1 g of degraded sodium alginate, 0.25 g of sucrose, and 0.45 g of sorbitol; the sodium alginate is degraded by exposing powdered sodium alginate to 25-53 kGy of γ irradiation (as detailed in Table 3 below). 0.8 g of the oligosaccharide powder is gradually added to 10 ml of the divalent cation solution, and stirred for 15 min at room temperature to obtain composition 9-14 for submucosal injection.

TABLE 3

| γ irradiation (kGy) | Calcium lactate (g) | | |
|---|---|---|---|
| | 0.01 (0.1% w/v) | 0.02 (0.2% w/v) | 0.025 (0.25% w/v) |
| 25 | Composition 9 | Composition 10 | Composition 6 |
| 32 | Composition 11 | Composition 12 | Composition 7 |
| 37 | Composition 1 | Composition 3 | Composition 4 |
| 53 | Composition 13 | Composition 14 | Composition 8 |

Analytical Methods

Viscosity test was conducted at 25° C. by using a rotational viscometer (Brookfield, DVE), with sample chamber model SC4-13R(P) and spindle model SC4-18.

Injection pressure was measured by using an injector comprised of a 23G endoscope long injection needle (160 mm) connected to a 3 mL syringe. To conduct the measurement, the injector with the syringe filled with a test composition was fixed to a texture analyzer (JISC, JSH-1000), which applied a force to the piston of the injector at a constant speed of 60 mm/min. The force needed to discharge the test composition out of the endoscope injection needle at 25° C. was defined as the injection pressure.

Diffusibility is examined by placing a drop of the composition on a filter paper using a dropper, and observing the changes in droplet shape after 5 min.

Submucosa elevating capacity is evaluated by using injecting 5 ml of the composition into the submucosa of an extracted porcine colon, and measuring the heights of the elevated submucosa before and after needle removal.

Evaluation

I. Effect of Divalent Cation Concentration on Viscosity and Injection Pressure of the Compositions As shown in Table 4, viscosity and injection pressure of compositions 1-5 increased with the concentration of calcium lactate in the compositions. Interestingly, as exemplified in the test results of compositions 4 and 5, when a divalent cation solution containing at least 0.25% of calcium lactate was combined with oligosaccharide powder exposed to 37 kGy of γ irradiation, a remarkable increase in viscosity, reaching over 1000 cP, was observed; whereas the injection pressure only showed a steady increase. In other words, when a particular amount of calcium lactate was added to the compositions, the increase in injection pressure was shown to be unproportional to that in viscosity. The observation was indicative of a pseudoplastic behavior, also known as shear thinning in non-Newtonian fluids.

TABLE 4

| Composition | Calcium lactate (g) | Viscosity (cP) | Injection Pressure (kgf) |
|---|---|---|---|
| Experiment Groups | | | |
| 1 | 0.01 (0.1% w/v) | 6.42 | 0.82 |
| 2 | 0.015 (0.15% w/v) | 7.70 | 0.97 |
| 3 | 0.02 (0.2% w/v) | 46.4 | 1.76 |
| 4 | 0.025 (0.25% w/v) | >1000 | 2.84 |
| 5 | 0.03 (0.3% w/v) | >1000 | 5.01 |
| Control Groups | | | |
| Normal saline | | <1 | 0.2 |
| 10% Glycerol | | <1 | 0.2 |
| 0.4% Hyaluronic acid | | 320 | 2.83 |

II. Effect of Irradiation Dose on Viscosity and Injection Pressure of the Compositions As shown in Table 5, injection pressure of compositions 4 and 6-8 decreased as the dose of γ irradiation increased; meanwhile, all three compositions were shown to be highly viscous. The result suggested that prior to mixing with a divalent cation solution containing 0.25% w/v of calcium lactate, the oligosaccharide powder needs to be exposed to at least 32 kGy γ irradiation, in order for the resulting compositions to exhibit a pseudoplastic behavior.

TABLE 5

| Composition | γ irradiation (kGy) | Viscosity (cP) | Injection Pressure (kgf) |
|---|---|---|---|
| 6 | 25 | >1000 | 6.03 |
| 7 | 32 | >1000 | 3.15 |
| 4 | 37 | >1000 | 2.89 |
| 8 | 53 | >1000 | 2.67 |

III. Correlation Between Divalent Cation Concentration and Irradiation Dose and Effect on Injection Pressure Thereof As discussed above, compositions having a pseudoplastic behavior are high in viscosity (e.g., over 1000 cP) and low in injection pressure (e.g., 2.5-4 kgf). Accordingly, the injection pressure being greater than 2.5 kgf is indicative of pseudoplasticity of the compositions. As demonstrated in FIG. 1, examination of the properties of compositions 9-14 showed that, to obtain compositions having an injection pressure of greater than 2.5 kgf, higher dose of γ irradiation for polysaccharide degradation and higher calcium lactate concentration in the divalent cation solution were required. For example, when the γ irradiation dose applied to sodium alginate was greater than 32 kGy, the divalent cation solution required at least 0.25% w/v of calcium lactate; likewise, when the γ irradiation dose for sodium alginate was less than 32 kGy, the required calcium lactate concentration was at least 0.1% w/v.

IV. Diffusibility of the Compositions

Figure 2A:
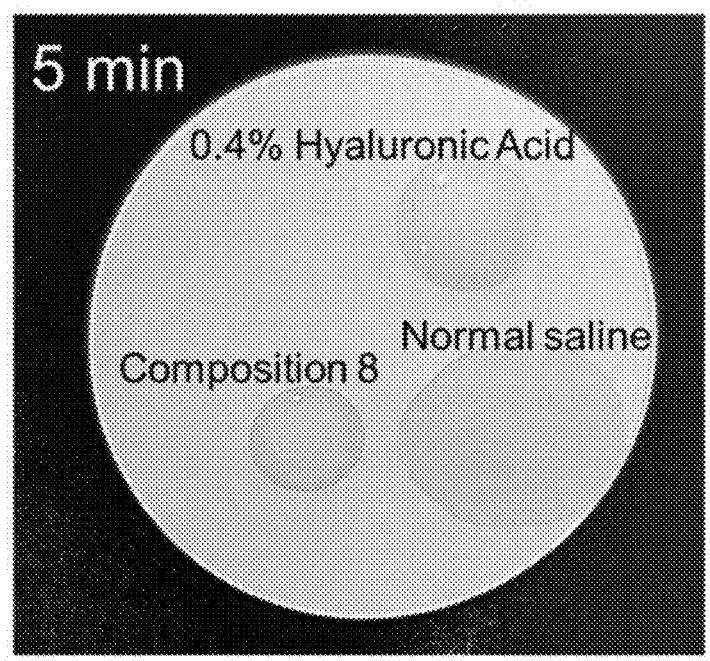
FIG. 2A is a microscopic image of droplets formed by the composition in accordance with an embodiment of the present disclosure.
Figure 2B:
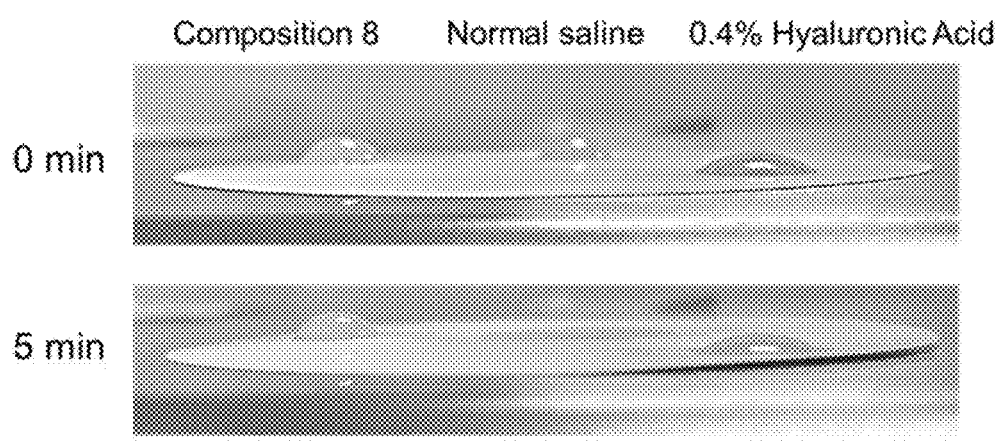
FIG. 2B is a photo image showing a side view of the droplets in FIG. 2A.

As shown in FIGS. 2A-2B, composition 8 was less prone to spread than hyaluronic acid and saline, demonstrating a noticeably better uplifting potential.

V. Submucosa Elevating Capacity

Figure 3:
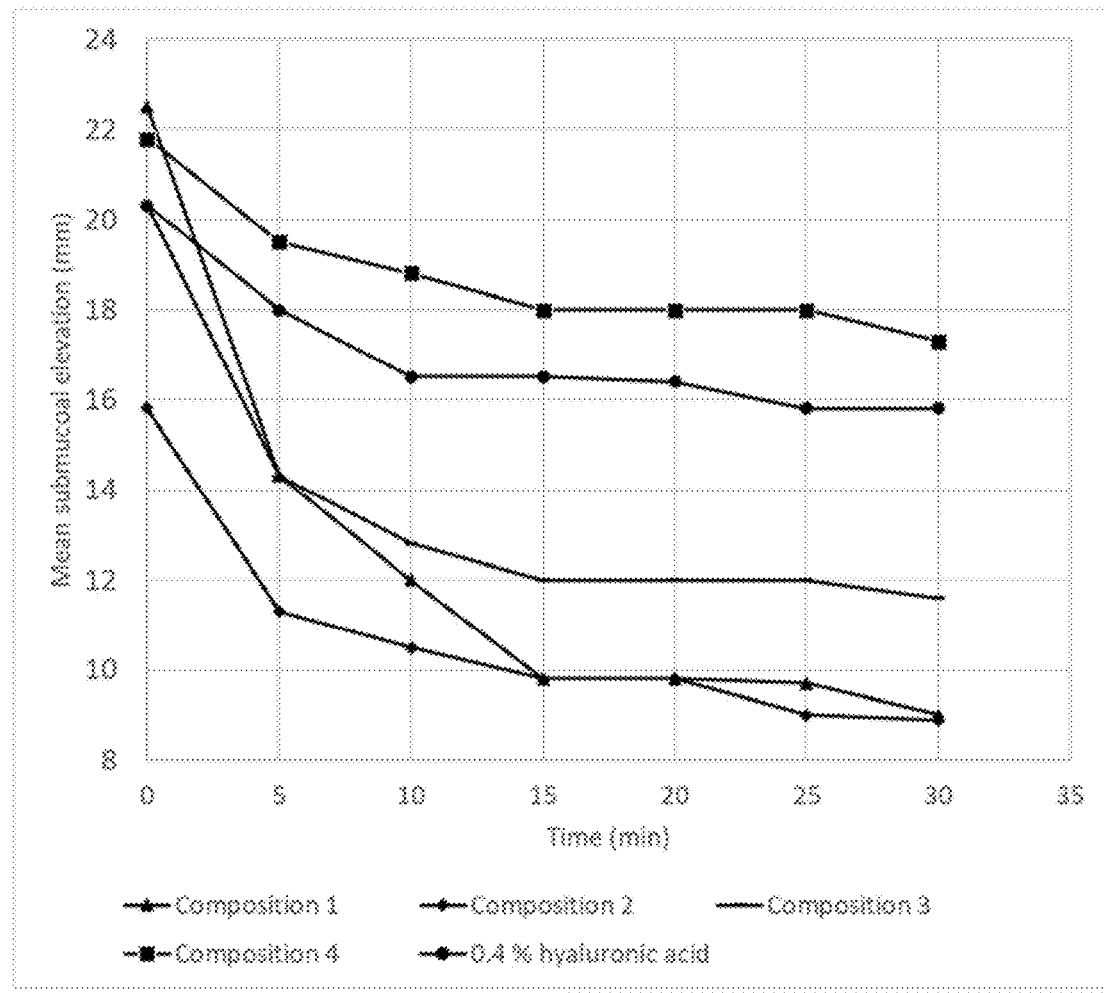
FIG. 3 is a line plot showing the time-dependent changes in height of mucosa elevated by the compositions in accordance with the embodiments of the present disclosure.
Figure 4A:
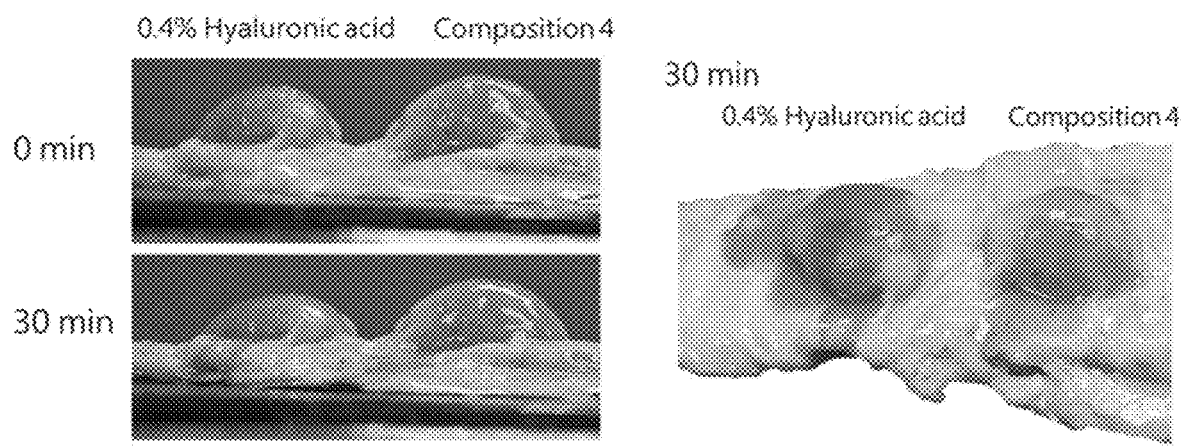
FIGS. 4A and 4B are photo images showing side and perspective views of submucosa elevated by the compositions according to the embodiments of the present disclosure.
Figure 4B:
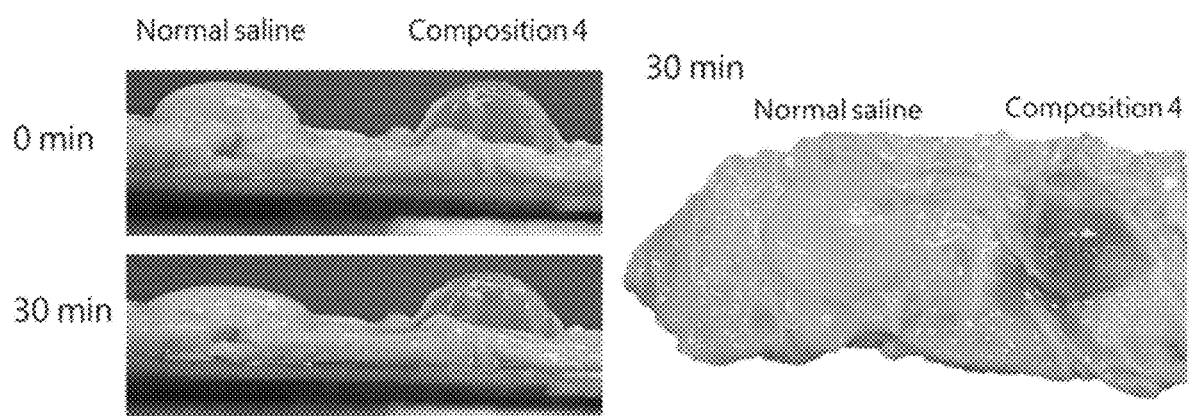

As shown in FIGS. 3 and 4A-4B, compositions 1-4 were capable of maintaining a cushion for at least 30 min, exhibiting an excellent submucosa elevating capacity.

The embodiments of the present disclosure provide a composition having pseudoplastic properties suitable for submucosal injection and elevation. The composition may be provided as a single solution, or have the divalent cation solution and the oligosaccharide powder separately packaged. The present disclosure presents an effective and easy-to-use solution for endoscopic resection.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A composition for submucosal injection, comprising:
   a divalent cation; and
   an oligosaccharide obtained by exposing powdered polysaccharides to irradiation, heat, ultrasound, or ultraviolet radiation, wherein viscosity of the composition is greater than 1000 cP, and injection pressure of the composition falls within a range of 2.5-4 kgf.

2. The composition according to claim 1, wherein the oligosaccharide is obtained by exposing the powdered polysaccharides to 25-100 kGy of gamma (γ) irradiation, 160-200° C. of heat, 100-280 nm of UV-C light, or 20-60 kHz of ultrasound.

3. The composition according to claim 1, wherein the divalent cation comprises at least one divalent cation selected from a group consisting of $Ca^{2+}$, $Mg^{2+}$, $Fe^{2+}$, $Cu^{2+}$, $Ba^{2+}$, and $Zn^{2+}$.

4. The composition according to claim 1, wherein a concentration of divalent cation in the composition falls within a range of 0.1-0.5% w/v.

5. The composition according to claim 1, wherein the oligosaccharide comprises at least one member selected from a group consisting of degraded sodium alginate, degraded xanthan gum, degraded dextran, degraded welan gum, degraded gellan gum, and degraded diutan gum.

6. The composition according to claim 1, wherein a concentration of the oligosaccharide in the composition falls within a range of 0.5-2% w/v.

7. The composition according to claim 1, further comprising a physiologically acceptable excipient.

8. A composition for submucosal injection, comprising:
a divalent cation solution; and
an oligosaccharide powder obtained by exposing powdered polysaccharides to irradiation, heat, ultrasound, or ultraviolet radiation,
wherein the divalent cation solution and the oligosaccharide powder are separately packaged, and when the divalent cation solution is mixed with the oligosaccharide powder, viscosity of the composition is greater than 1000 cP, and injection pressure of the composition falls within a range of 2.5-4 kgf.

9. The composition according to claim 8, wherein the oligosaccharide powder is obtained by exposing the powdered polysaccharides to 25-100 kGy of γ irradiation, 160-200° C. of heat, 100-280 nm of UV-C light, or 20-60 kHz of ultrasound.

10. The composition according to claim 8, wherein the divalent cation solution comprises at least one divalent cation selected from a group consisting of $Ca^{2+}$, $Mg^{2+}$, $Fe^{2+}$, $Cu^{2+}$, $Ba^{2+}$, and $Zn^{2+}$.

11. The composition according to claim 8, wherein a concentration of divalent cations in the divalent cation solution falls within a range of 0.1-0.5% w/v.

12. The composition according to claim 8, wherein the oligosaccharide powder comprises at least one member selected from a group consisting of degraded sodium alginate, degraded xanthan gum, degraded dextran, degraded welan gum, degraded gellan gum, and degraded diutan gum.

13. The composition according to claim 8, wherein a concentration of oligosaccharides in the composition falls within a range of 0.5-2% w/v.

14. The composition according to claim 8, further comprising a physiologically acceptable excipient for the divalent cation solution or the oligosaccharide powder.

15. A method for preparing a composition for submucosal injection, comprising steps of:
providing a divalent cation solution;
providing an oligosaccharide powder obtained by exposing powdered polysaccharides to irradiation, heat, ultrasound, or ultraviolet radiation; and
mixing the oligosaccharide powder with the divalent cation solution to obtain the composition for submucosal injection,
wherein viscosity of the composition is greater than 1000 cP and injection pressure of the composition falls within a range of 2.5-4 kgf.

16. The method according to claim 15, wherein the oligosaccharide powder is obtained by exposing the powdered polysaccharides to 25-100 kGy of γ irradiation, 160-200° C. of heat, 100-280 nm of UV-C light, or 20-60 kHz of ultrasound.

17. The method according to claim 15, wherein the divalent cation solution comprises at least one divalent cation selected from a group consisting of $Ca^{2+}$, $Mg^{2+}$, $Fe^{2+}$, $Cu^{2+}$, $Ba^{2+}$, and $Zn^{2+}$.

18. The method for submucosal injection according to claim 15, wherein a concentration of divalent cations in the divalent cation solution falls within a range of 0.1-0.5% w/v.

19. The method according to claim 15, wherein the oligosaccharide powder comprises at least one member selected from a group consisting of degraded sodium alginate, degraded xanthan gum, degraded dextran, degraded welan gum, degraded gellan gum, and degraded diutan gum.

20. The method according to claim 15, wherein a concentration of oligosaccharides in the composition falls within a range of 0.5-2% w/v.

* * * * *